United States Patent [19]

Maeda et al.

[11] Patent Number: 5,389,366
[45] Date of Patent: Feb. 14, 1995

[54] NEOCARZINOSTATIN DERIVATIVE COMPOSITION FOR ORAL ADMINISTRATION

[75] Inventors: Hiroshi Maeda, 631-3, Aza-Tamukae, Hotakubohon-Machi, Kumamoto City, Kumamoto Pref.; Fujio Suzuki, Kumamoto; Kiichiro Oka, Kumamoto; Shohei Tanaka, Kumamoto, all of Japan

[73] Assignees: Yamanouchi Pharmaceutical Co., Ltd., Tokyo; Hiroshi Maeda, Kumamoto; Kuraray Co., Ltd., Kurashiki; Kayaku Antibiotics Research Co., Ltd., Tokyo, all of Japan

[21] Appl. No.: 61,338

[22] Filed: May 17, 1993

Related U.S. Application Data

[63] Continuation of Ser. No. 751,175, Aug. 28, 1991, abandoned, which is a continuation of Ser. No. 414,388, Sep. 29, 1986, abandoned, which is a continuation-in-part of Ser. No. 78,942, Jul. 29, 1987, abandoned.

[30] Foreign Application Priority Data

Sep. 19, 1986 [JP] Japan ................................. 61-221166

[51] Int. Cl.⁶ ............................................. A61K 31/74
[52] U.S. Cl. ............................ 424/78.33; 424/78.08; 514/2
[58] Field of Search .................. 424/78; 514/2, 12; 530/350; 435/886

[56] References Cited

U.S. PATENT DOCUMENTS

| | | | |
|---|---|---|---|
| 3,085,994 | 4/1963 | Muskat | 260/78.5 |
| 3,121,043 | 2/1964 | Tobin et al. | 167/82 |
| 3,245,933 | 4/1966 | Muskat | 260/29.6 |
| 3,334,022 | 8/1967 | Ishida et al. | 195/80 |
| 4,156,719 | 5/1979 | Sezaki et al. | 424/118 |
| 4,182,752 | 1/1980 | Maeda et al. | 424/78 |
| 4,659,696 | 4/1987 | Hirai et al. | 514/15 |
| 4,670,419 | 6/1987 | Uda et al. | 514/16 |
| 4,758,580 | 7/1988 | Numasaki et al. | 514/345 |
| 5,026,772 | 6/1991 | Kobayashi et al. | 525/541 |

FOREIGN PATENT DOCUMENTS

| | | |
|---|---|---|
| 0087957 | 9/1983 | European Pat. Off. . |
| 0136791 | 4/1985 | European Pat. Off. . |
| 0136792 | 4/1985 | European Pat. Off. . |
| 2114885 | 1/1983 | United Kingdom . |

OTHER PUBLICATIONS

Chemical Abstracts, 89:209295d, Neocarzinostatin Derivatives, H. Maeda et al., vol. 89, DE OS 2,813,017.
Chemical Abstracts, 97:272t, vol. 97, 1982, "In Vitro Mode of Action, Pharmacokinetics . . .", J. Takeshita, et et al., Gann (1982), 73(2), 278–84, p. 26.
Chemical Abstracts, 98:137338j, vol. 98, 1983, "Augumentation of Tumoritropicity . . .", H. Maeda et al., Igaku no Ayumi (1983), 124(1), 25–8.
Chemical Abstracts, 91:162995j, vol. 91, 1979, "A Lipophilic Derivative of Neocarzinostation . . .", H. Maeda et al., Int. J. Pept. Protein Res., 1979, 14(2), 81–7, (Eng.).
Wilson, C. O., et al., Eds.. Textbook of Organic Medicinal and Pharmaceutical Chemistry, 7th Ed., J. B. Lippincott Co., Pub., pp. 336–339, (1977).
Iwai, K. et al., "Use of Oily Contrast Medium For Selective Drug Targeting . . .", Cancer Research, 44, pp. 2115–2121 (May 1984).
Meienhofer, J., Ed., "Primary Structure of Neocarzinostatin, An Antitumor Protein", Science, vol. 178, (Nov. 24, 1972), pp. 875–876.
Ishida, N., et al., "Neocarzinosstatin, An Antitumor Antibiotic of High Molecular Weight", The Journal Of Antibiotics, Ser. A, vol. XVIII, No. 2, (Mar. 1965), pp. 68–76.
Miziorko, H., et al., "Spinach Leaf Phosphoenolpyruvate Carboxylase: Purification . . .", Archives of Biochemistry and Biophysics, vol. 163, (1974), pp. 378–389.

Primary Examiner—G. S. Kishore
Attorney, Agent, or Firm—Spencer, Frank & Schneider

[57] ABSTRACT

A composition for oral administration to cancer patients includes a neocarzinostatin derivative and from 0.1 and 100 ml per mg of the neocarzinostatin derivative of at least one fatty acid glyceride which has from 6 to 20 carbon atoms and which is noniodized. The composition is effective in the treatment of cancer by oral administration, including a solid cancerous tumor.

4 Claims, 2 Drawing Sheets

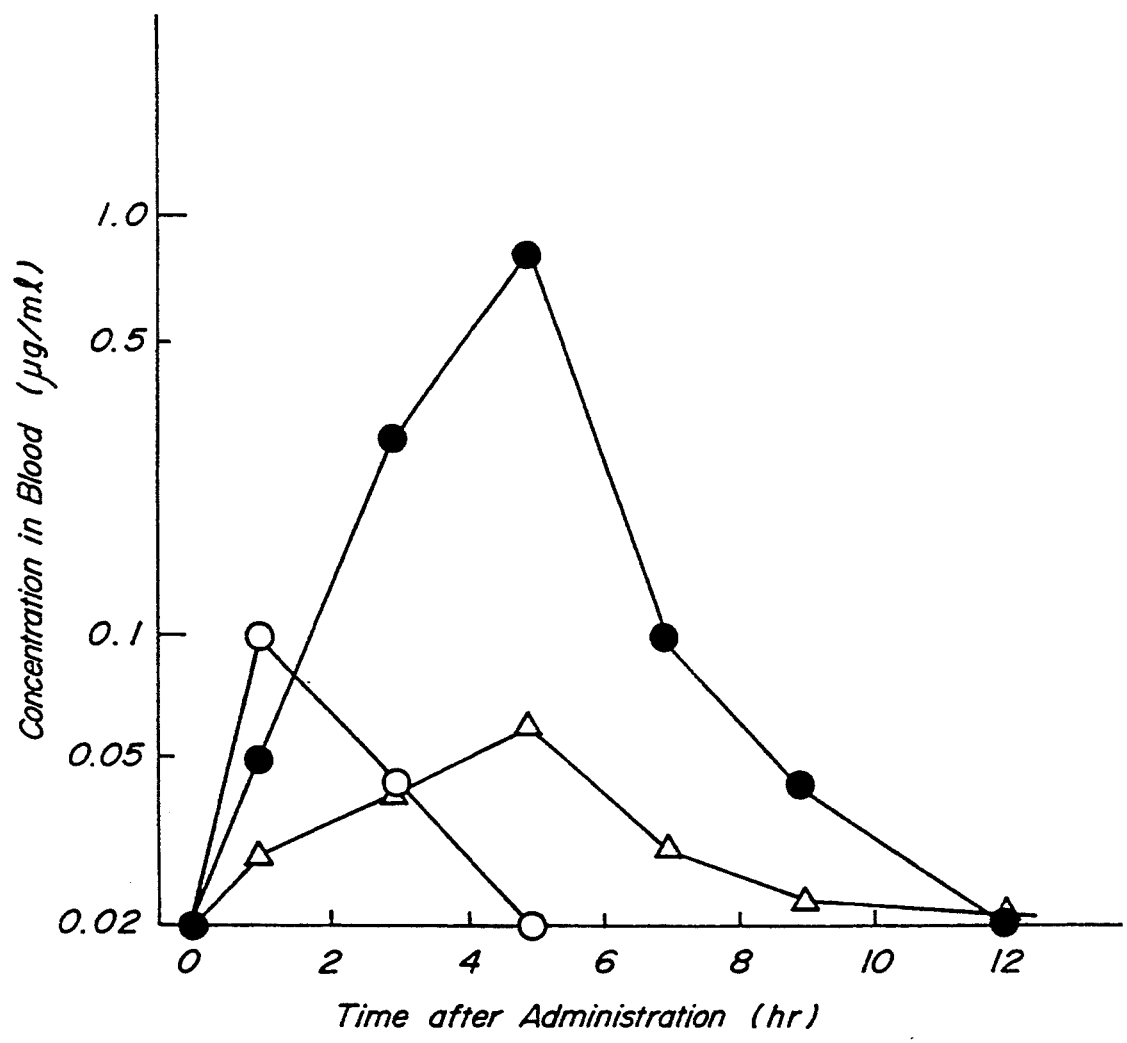

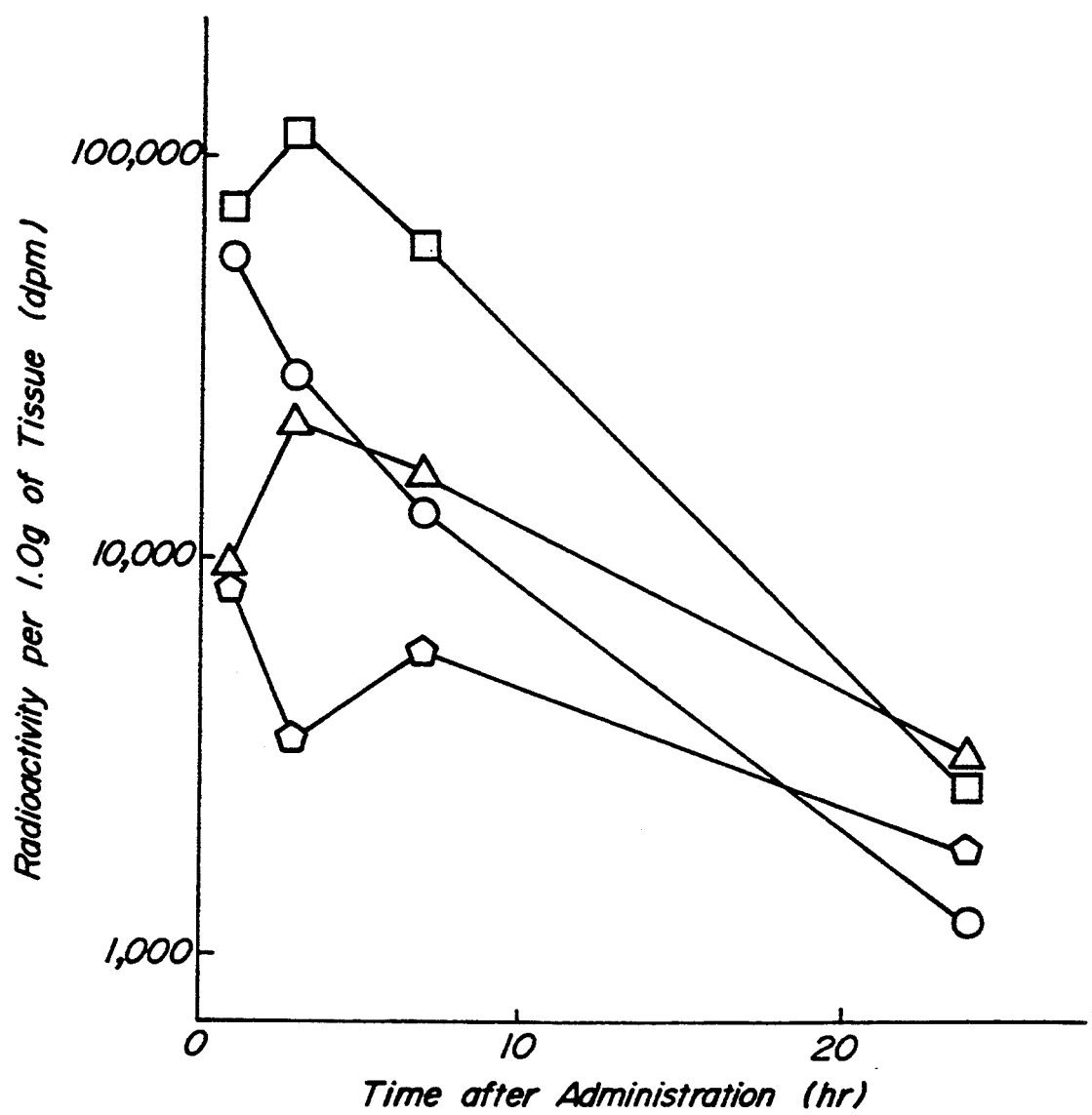
FIG_2

NEOCARZINOSTATIN DERIVATIVE COMPOSITION FOR ORAL ADMINISTRATION

This application is a continuation of application Ser. No. 07/751,175, filed Aug. 28, 1991, now abandoned which is a continuation of application Ser. No. 07/414,388, filed Sep. 29, 1989, abandoned, which is a continuation-in-part of application Ser. No. 07/078,942, filed Jul. 29, 1987, abandoned.

BACKGROUND OF THE INVENTION

1. Field of the Invention

This invention relates to a composition for oral administration comprised of a neocarzinostatin derivative (hereinafter abbreviated as SMANCS) having styrene-maleic acid copolymeric residue(s).

2. Related Art Statement

SMANCS is a derivative of neocarzinostatin (hereinafter abbreviated as NCS) is a proteinaceous anticancer substance, wherein carbonyl groups of a styrene-maleic acid copolymer (hereinafter abbreviated as SMA) are bonded to two primary amino groups existent in the molecule of NCS through an acid amide. That is, it is a cancerocidal substance having a reduced toxicity and improved pharmacological properties as compared with those of NCS.

It is considered that SMANCS cannot be orally administered because it is decomposed gastrically and intestinally by digestive juice which is likewise composed of high molecular weight biogenic peptides and proteins, and is poorly absorbed. For this end, therefore, SMANCS is generally administered by an injection. In the latter case, however, pain is unavoidable to patients and self administration is impossible. Furthermore, for daily injections, patients need to be hospitalized, and this situation results in greater treatment expense. Therefore, a great demand exists to develop a SMANCS composition for oral administration.

Heretofore, it has been attempted to provide such a preparation of biogenic peptide for oral administration, see for instance, Japanese laid open Patent Application No. 61-93,129 which discloses an orally administering preparation comprising a lipotropic medium such as mineral oil or the like and a gastrocolic absorption accelerator such as sodium salicylate or the like). On the other hand, since SMANCS is obtained by bonding SMA as a polymer to NCS as a high molecular weight biogenic peptide, as previously mentioned, it is a very special cancerocidal substance possessing properties of a peptide and properties of a polymer, so that the preparation for oral administration attempted in the biogenic peptide cannot be applied to SMANCS as it is. Actually, the inventors have tried to prepare SMANCS with an oily substance, such as fatty acid, fatty acid alkyl ester, cholesterol, mineral oil or the like for oral administration, but this attempt was yet unsuccessful.

SUMMARY OF THE INVENTION

The inventors have made various studies with respect to SMANCS compositions capable of developing a high anticancer activity by oral administration and found that the aforementioned problems are solved by using an oily composition composed of a combination of SMANCS and a particular fatty oil.

That is, the invention provides a composition for oral administration comprising SMANCS and a medium to long chain fatty acid glyceride. And also, the invention provides a composition for oral administration comprising SMANCS, a medium to long chain fatty acid glyceride and an amphiphilic agent.

Here, SMANCS is a neocarzinostatin derivative represented by the following formula (A):

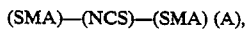

wherein (NCS) is a divalent neocarzinostatin residue in which one hydrogen atom is removed from each of the primary amino group in alanine residue at the N-terminal of neocarzinostatin and that in lysine residue at 20th position from the N-terminal of neocarzinostatin and (SMA) is a monovalent styrene-maleic acid copolymeric residue, which may be partially half-esterified and consists of structural units for 1) styrene residue

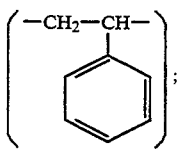

2) residue having the following formula in which a hydroxyl group of one carboxyl group in maleic acid residue is removed and linked to be bonded to the neocarzinostatin residue

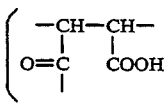

wherein the linkage of carbon atom in carbonyl group bonds to the neocarzinostatin residue); and 3), a) maleic acid residue

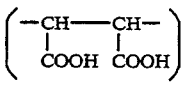

or b) half-esterified maleic acid residue

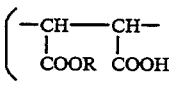

in which R is an alcohol residue wherein hydroxyl group is removed from an alkanol having 1 to 4 carbon atoms, ethylene glycol monoalkyl ether in which the alkyl group has 1 to 2 carbon atoms or glycerine dialkyl ether wherein the alkyl group has 1 to 2 carbon atoms) and maleic acid residue

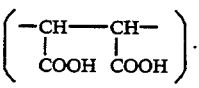

BRIEF DESCRIPTION OF THE DRAWINGS

The invention will be described with reference to the accompanying drawings, wherein:

FIG. 1 is a graph showing a change of Bu-SMANCS concentration in blood with time after oral administration of the composition according to the invention; and FIG. 2 is a graph showing a change of intracorporeal distribution of $^{14}C$ glycine labeled Bu-SMANCS with time after oral administration.

DESCRIPTION OF THE PREFERRED EMBODIMENTS

The details of SMANCS are disclosed in Japanese laid open Patent Application Nos. 60-75,432 and 60-75,499, a typical example of which is a compound wherein the styrene-maleic acid copolymeric residue referred to as (SMA) is a half-butyl esterified styrene-maleic acid copolymeric residue (hereinafter abbreviated as Bu-SMANCS).

The medium to long chain fatty acid glyceride is a mono-, di- or tri-glyceride of saturated or unsaturated fatty acid having a carbon number of 6 to 20. As the fatty acid glyceride, use may be made of mono-, di- and tri-glycerides of caprylic acid, captic acid, lauric acid, myristic acid, palmitic acid, oleic acid, linoleic acid, linolenic acid and so on. These fatty acid glycerides may be used alone or in admixture. Further, the fatty acid glyceride may be natural, synthetic or semi-synthetic substance. In general, it is convenient to use natural vegetable oils. As the preferred vegetable oil used in the invention, mention may be made of olive oil (oleic acid: 70~85%, linoleic acid: 4~12%, palmitic acid: 7~15%), maize oil (linoleic acid: 40~60%, palmitic acid: 25~45%), sesame oil (oleic acid: 35~46%, linoleic acid: 35~48%), tsubaki oil, coconut oil (lauric acid: 45~52%, capric acid: 4~12%, caprylic acid: 6~10%), palm oil and so on. Moreover, commercially available vegetable oils may be used as they are. The commercially available medium chain fatty acid triglyceride includes Panasate 875 ®, Panasate 810 ® and Panasate 800 ® (registered trade name) made by Nippon Oil and Fats Co., Ltd. (content of caprilic acid: 10~100%), ODO ® (registered trade name) made by Nisshin Seiyu K.K. (content of caprilic acid: 67%) and the like. The medium chain fatty acid monoglyceride includes Homoteks PT ® (registered trade name) made by Kao Corporation (content of capric acid: about 60%) and so on. As a mixture of medium chain fatty acid monoglyceride and diglyceride, use may be made of Witafrol ® (registered trade name) made by Dinamit Novel Corporation and so on. As the long chain fatty acid triglyceride, use may be made of commercially available olive oil, safflower oil and other edible oils.

Further, there are some cases in which iodized oil, strong iodized oil (the 9th Japanese Pharmacopeia: iodized vegetable oil) or iodized poppy seed oil fatty acid ethylester (Lipiodol Ultra-Fluide ® made by Andre Guerbet) which is a contrast agent for roentgenography is used as a fats and oils in oily formulation of Antitumor substance (cf. e.g. U.S. Pat. No. 4,578,391, from column 1, penultimate line to column 2, line 3). However, such iodized oils are not suitable for the present invention (cf. FIG. 1).

The amphiphilic agent is a non-toxic substance possessing hydrophilicity and lipophilicity, which includes, for example, a natural ampholytic surfactant, a polyglycerine fatty acid ester, a polyoxyethylenesorbitan fatty acid ester (Tween series), a sorbitan fatty acid ester (Span series), a polyethylene glycol and so on.

As the natural ampholytic surfactant, use may be made of soybean phospholipid, yolk lecithin and analogous compounds such as phosphatidylcholine made by Nippon Oil and Fats Co., Ltd., yolk lecithin, soybean lecithin, phosphatidylethanolamine and so on. Further, Unigli ® (registered trade name) made by Nippon Oil and Fats Co., Ltd. may be used as a polyglycerine fatty acid ester, and Tween 20 ® (registered trade name, sold by Wako Junyaku Kogyo K.K.) may be used as a polyoxyethylenesorbitan fatty acid ester, and Span 20 ® (registered trade name, sold by Wako Junyaku Kogyo K.K.) may be used as a sorbitan fatty acid ester, and PEG 6000 (trade name) may be used as a polyethylene glycol. Besides this, sodium lauryl sulfate may be used as an anion surfactant, and benzalkonium chloride and benzethonium chloride, Azone ® (registered trade name, made by Nelson Res. & Dev. Co.) may be used as a cation surfactant.

In the preparation of the composition according to the invention, a lyophilized powder of SMANCS is added to the medium to long chain fatty acid glyceride and uniformly dispersed thereinto. When using the amphiphilic agent, it may be added at any stage. That is, SMANCS and the amphiphilic agent may be mixed in water and then lyophilized in the production of the SMANCS lyophilized powder, or the amphiphilic agent may be added to the medium to long chain fatty acid glyceride before mixing with the SMANCS lyophilized powder. This is applicable to a case of using two or more amphiphilic agents.

An example of preparation of the composition according to the invention is as follows:

(a) The lyophilized powder of SMANCS is added to the medium to long chain fatty acid glyceride previously mixed or not mixed with the amphiphilic agent and then uniformly dispersed thereinto to form an oily composition. Moreover, the lyophilized powder of SMANCS as a starting material is obtained by lyophilizing an aqueous solution of SMANCS in a usual manner.

(b) SMANCS and the amphiphilic agent are mixed in water. Preferably, the aqueous solution of SMANCS is mixed with the aqueous solution of amphiphilic agent as equal parts by weight. Then, the resulting mixture is lyophilized and added to the medium to long chain fatty acid glyceride previously mixed or not mixed with the amphiphilic agent and uniformly dispersed thereinto to form an oily composition.

In the uniform dispersion, the shake-agitation is continued until a sufficient dispersed state is visually confirmed. For instance, the shake-agitation is carried out by an ultrasonic treatment using an ultrasonic generator. Moreover, in order to enhance the uniform dispersibility in the composition according to the invention, a lower alcohol, such as ethanol or the like, may previously be added to the medium to long chain fatty acid glyceride.

The above procedures are carried out at room temperature or under cooling, e.g., in an ice-water bath, whereby the composition according to the invention can be prepared.

According to the invention, the amount of the fatty acid glyceride used is about 0.1~100 ml, preferably 0.5~5 ml per 1 mg of SMANCS. The addition of the amphiphilic agent is not necessarily required, but it provides a good oil-wetting effect to increase the dispersion solubility and hence form a stable composition, and brings about the absorption promoting effect. The amount of the amphiphilic agent added is changed in accordance with the kind thereof, but it is usually 0.01~0.1 ml in case of a liquid agent and 0.05~5 mg in case of a solid agent per 1 mg of SMANCS. Moreover, the amount of the lower alcohol added for enhancing the dispersibility is 0.01~0.5 ml, preferably 0.05~0.2 ml per 1 mg of SMANCS.

The oily composition according to the invention is stable physically and chemically. That is, sediments are not observed even when the composition is subjected to a centrifugal separation at room temperature and 5,000 rpm for 15 minutes or is left to stand at 37° C. for one month. Further, the anticancer activity of SMANCS is not reduced even when the composition is stored at 4° C. or room temperature under shading for at least 3 months. Moreover, even when the composition is subjected to a temperature change of 4° C. and room temperature every 24 hours ten times, no change is visually observed and the titer is stable.

As mentioned above, the composition according to the invention has excellent stability and makes it possible to administer SMANCS via a pathway other than by injection, whereby the utility of SMANCS as an anticancer agent is enhanced.

The effect of the composition according to the invention will concretely be described by the following animal experiments.

(I) Test for anticancer activity

The anticancer activities against an RL ♂ 1 murine solid tumor, an S-180 murine solid tumor, an S-180 murine ascites-type tumor and a Meth A murine solid tumor are set forth with their experimental methods.

(1) Inhibition effect against an RL ♂ 1 murine solid tumor

Experimental method

After $10^6$ RL ♂ 1 tumor cells were subcutaneously transplanted into a ventral side portion of BALB/c mouse(8 week age), a medication to be tested as mentioned later was administered to the mouse one time per day starting the day after the transplantation over a week. After 21 days from the tumor transplantation, the mouse was killed to measure the tumor weight.

The measured results are shown in the following Table 1.

TABLE 1

| Test medicine | Dose (ml/mouse) | Dose (mg/Kg) as Bu-SMANCS | Administration pathway | Tumor weight (mg) | Inhibition ratio (%) |
| --- | --- | --- | --- | --- | --- |
| Physiological saline (control) | 0.2 | | oral | 2,029 | — |
| ODO ® alone (control) | 0.2 | | oral | 2,034 | 0 |
| Bu-SMANCS* (control) | 0.1 | 0.1 | intravenous injection | 303 | 85 |
| Composition of Preparation Example 11 (drug concentration: 1.5 mg/ml) | 0.2 | 10.1 | oral | 816 | 60 |
| Composition of Preparation Example 11 (drug concentration: 0.15 mg/ml) | 0.2 | 1.0 | oral | 1,197 | 41 |

*Positive control for aqueous intravenous injection (drug concentration: 0.03 mg/ml)

(2) Inhibition effect against an S-180 murine solid tumor

Experimental method

After $10^6$ S-180 tumor cells were subcutaneously transplanted into a ventral side portion of ddY mouse (1 group: 10 mice), a medication to be tested was administered to the mouse one time per day starting the day after the transplantation over a week. In 17 days after the transplantation, the tumor portion was extirpated to measure the weight.

The measured results are shown in the following Table 2.

TABLE 2

| Test medicine | Dose (ml/mouse) | Dose (mg/Kg) as Bu-SMANCS | Administration pathway | Tumor weight (mg) | Inhibition ratio (%) |
| --- | --- | --- | --- | --- | --- |
| Physiological saline (control) | 0.2 | | oral | 776 | — |
| ODO ® alone (control) | 0.2 | | oral | 744 | 4 |
| Bu-SMANCS* (control) | 0.1 | 0.1 | intravenous injection | 64 | 92 |
| Bu-SMANCS** (control) | 0.2 | 10.1 | oral | 795 | 0 |
| Composition of Preparation Example 11 (drug concentration: 1.11 mg/ml) | 0.2 | 1.0 | oral | 107 | 86 |

*Positive control for aqueous intravenous injection (drug concentration: 0.01 mg/ml)
**Positive control for aqueous intravenous injection (drug concentration: 1.5 mg/ml)

(3) Inhibition effect against S-180 murine ascites-type tumor

Experimental method

After $10^6$ S-180 tumor cells were intra-abdominally transplanted into ddY mouse (8 week age), a medication to be tested was administered to the mouse one time per day starting the day after the transplantation over a week. In 12 days after the transplantation, the mice were killed to measure the tumor weight.

The measured results are shown in the following Table 3.

TABLE 3

| Test medicine | Dose (ml/mouse) | Dose (mg/Kg) as Bu-SMANCS | Administration pathway | Tumor weight (mg) | Inhibition ratio (%) |
| --- | --- | --- | --- | --- | --- |
| Physiological saline (control) | 0.2 | | oral | 1,260 | — |
| ODO ® alone (control) | 0.2 | | oral | 1,348 | 0 |
| Bu-SMANCS* (control) | 0.1 | 0.5 | intravenous injection | 911 | 28 |
| Composition of Preparation Example 11 (drug concentration: 1.11 mg/ml) | 0.2 | 7.4 | oral | 951 | 25 |
| Composition of Preparation Example 11 (drug concentration: | 0.2 | 2.5 | oral | 1,001 | 21 |

TABLE 3-continued

| Test medicine | Dose (ml/ mouse) | (mg/Kg) as Bu-SMANCS | Administration pathway | Tumor weight (mg) | Inhibition ratio (%) |
| --- | --- | --- | --- | --- | --- |
| 0.375 mg/ml) | | | | | |

*Positive control for aqueous intravenous injection (drug concentration: 0.15 mg/ml)

(4) Inhibition effect against Meth A murine solid tumor

After 106 Meth A murine tumor cells were subcutaneously transplanted into a ventral side portion of BALB/c mouse (8 week age), a medication to be tested was administered to the mouse one time per day starting the day after transplantation over a week. In 14 days after transplantation, the mice were killed to measure the tumor weight.

The measured results are shown in the following Table 4.

TABLE 4

| Test medicine | Dose (ml/ mouse) | (mg/Kg) as Bu-SMANCS | Administration pathway | Tumor weight (mg) | Inhibition ratio (%) |
| --- | --- | --- | --- | --- | --- |
| Physiological saline (control) | 0.2 | | oral | 240 | — |
| ODO ® alone (control) | 0.2 | | oral | 235 | 2 |
| Bu-SMANCS* (control) | 0.1 | 0.1 | intravenous injection | 6 | 98 |
| Composition of Preparation Example 11 (drug concentration: 1.5 mg/ml) | 0.2 | 10.0 | oral | 27 | 89 |
| Composition of Preparation Example 11 (drug concentration: 0.15 mg/ml) | 0.2 | 1.0 | oral | 137 | 43 |

*Positive control for aqueous intravenous injection (drug concentration: 0.03 mg/ml)

(II) Transport of oily Bu-SMANCS into the blood after the oral administration

The concentration of Bu-SMANCS in the blood was measured by bioassay or radioactivity analysis. The following results were obtained.

(1) Measurement of bioactivity (a) Test method and results using bacterium

To a mouse (ddY, 8 week age) was orally and forcedly administered 1.0 ml of the composition in Preparation Example 5 as mentioned later (containing 4 mg/ml of oily Bu-SMANCS) through a stainless stomach tube. After the administration, blood (or plasma) was taken out every time given and then the bioactivity of Bu-SMANCS in the blood was measured by using Micrococcus luteus according to a method described by H. Maeda, J. Takeshita and A. Yamashita, Eur. J. Cancer, 16, pp 723-731, 1980. At 3 hours after the administration, the bioactivity in blood became maximum, and the drug concentration in blood equal to that through intravenous injection was obtained. From this fact, it is considered that the orally administered oily Bu-SMANCS is easily absorbed by a bowel and distributed via the general circulation and lymphatic system in the whole body. The concentration of Bu-SMANCS in plasma after 3 hours of administration is shown in the following Table 5.

TABLE 5

| Time after administration | Drug concentration in plasma* |
| --- | --- |
| 3 hours | 2.5 ug/ml |

*: based on bioactivity, use of original BU-SMANCS as standard (b) Test method and results using culture cell To a mouse (ddY, 8 week age) fasted over more than 12 hours was orally and forcedly administered 1.0 ml of a composition in Preparation Example 28 as mentioned later (containing 4 mg/ml) of Bu-SMANCS) or 1.0 ml of an aqueous solution of Bu-SMANCS in physiological saline (containing 4 mg/ml of Bu-SMANCS) as an aqueous intravenous injection positive control (PBS: phosphate buffered 0.15M saline) through a stainless stomach tube. After the administration, 30 μl of blood was drawn from a tail vena of the mouse at 0, 1, 3, 5, 7, 9 or 12 hours and added to 300 μl of a culture medium containing culture cells. The culture cells were prepared by diluting EB virus-transformed B lymphoblastomid cells at logarithmic growth phase in the culture medium at a concentration of $2 \times 10^5$ cells/ml and pouring the resulting dilution into each of 96 holes in a plastic plate (Falcon) in an amount of 300 μl. After the addition of blood, the plate was cultured at 37° C. in an atmosphere containing 5% of $CO_2$ and 95% air. After two days of culture, they were stained with trypan blue and the number of living cells were counted, from which a survival rate was calculated. Then, the concentration of Bu-SMANCS in the blood was measured from the standard curve. The results are shown in FIG. 1, wherein mark ● shows results using the composition according to the invention and mark shows results using SMANCS in aqueous (PBS) form administered orally as control. Further, mark Δ shows results using the formulation obtained in comparative example described later (Lipiodol Ultra-Fluide solution of SMANCS). Two mice for each point were used.

As seen from FIG. 1, the composition according to the invention gave prolonged retension time of Bu-SMANCS in blood through oral administration as compared with the aqueous (PBS) oral administration as control. The oily formulation according to the invention gave much higher plasma concentration compared with the aqueous (PBS) form and Lipiodol Ultra-Fluide solution of SMANCS. Furthermore, the area under the curve of the concentration in the plasma is increased greatly to more than 10 fold. Thus, the formulation of comparative example is not effective, though it is oily an formulation.

(2) Activation analysis (i) Preparation of $^{14}C$ glycine labeled Bu-SMANCS 18.3 mg of Bu-SMANCS was dissolved in 1.0 g of distilled water, to which was added 19.9 mg of water-soluble carbodiimide and after 30 minutes, 0.1 mg of $^{14}C$ glycine (1.5 ml aqueous solution: New England Nuclear Corp., 113.0 m Ci/m mol) was added. The resulting solution was adjusted with an aqueous solution of 1M $NaHCO_3$ so as to make pH about 6 and reacted at room temperature for 1 hour with stirring. After the reaction was stopped by adding 1.0 ml of 1M acetic acid buffer solution (pH=6.0), the reaction product was desalted by a Sephadex ® G-25 column ($2.3 \times 10$ cm) and then lyophilized to obtain a fluffy sample (16.7 mg of $^{14}C$ glycine labeled Bu-SMANCS). It gave a specific radioactivity of 1.27μ Ci/mg, wherein one glycine was mainly introduced into one molecule of Bu-SMANCS. This single sample is a stable compound wherein glycine is bonded to a carboxyl group of Bu-SMANCS through an amide bond.

(ii) Animal experiment through oral administration

A composition of Preparation Example 2 as mentioned later was prepared by using the above $^{14}$C glycine labeled Bu-SMANCS. Then, 0.1 ml (0.64μ Ci) of this composition was forcedly and orally administered to a mouse (ddY♂, 8 week age) through a stainless stomach tube. After the administration, the mouse was killed at 1, 3, 7 or 24 hours to measure the radioactivity in plasma and major organs. The measured results are shown in FIG. 2, wherein mark Δ is the liver; O, the blood plasma; □, the kidney and ◊, the stomach. Moreover, the radioactivity is represented by dpm per 1.0 g of tissue. FIG. 2 shows that the composition according to the invention is efficiently transferred into the blood and each intracorporeal tissue in the aforementioned data of bioassay.

As mentioned above, the composition according to the invention exhibited an excellent anticancer effect through the oral administration.

As a clinical application to humans, the composition according to the invention is prepared into an appropriate formulation, such as a capsule, soft capsule, tablet, granule, liquid, suppository or the like, which is administered to a cancer patient by non-injection administration such as oral, intrarectal, intrathoracic or intraperitoneal administration.

The administration is carried out every day or every other day 1 to 5 times per day in such a manner that a dose per time of SMANCS is 0.1~100 mg. The composition according to the invention can be applied to a solid tumor as well as to a liquid tumor (leukemia) and to a ascitic tumor.

The preparation of the composition according to the invention will be explained with following examples. In these examples Bu-SMANCS is used as SMANCS, but similar results may be obtained by using the other SMANCS.

Preparation Method 1

To the lyophilized powder of Bu-SMANCS was added the medium to long chain fatty acid glycerides previously mixed with the amphiphilic agent, and the resulting mixture was shaken till dispersed completely as confirmed visually. In this case, the ultrasonic treatment was carried out by using a chip-type ultrasonic generator, Model UR-150P: Tomy Seiki K.K. The time required was no more than 30 seconds.

Preparation Method 2

40 mg of the amphiphilic agent was dissolved in 5 ml of distilled water by the ultrasonic treatment, and the aqueous solution of 1% ammonium carbonate was added dropwise to adjust the pH to about 8. The resulting solution was mixed with a solution of Bu-SMANCS powder (4 mg/ml) dissolved in an aqueous solution of 0.02% ammonium carbonate under ice cooling at an equal weight ratio under stirring, which was then lyophilized. The resulting lyophilized powder was added to the medium to long chain fatty acid glyceride and subjected to an ultrasonic treatment in ice for 30 seconds.

The composition according to the invention having a composite ratio shown in the Table 6 was obtained by the above preparation method 1 or 2.

TABLE 6

| Preparation Example No. | BU-SMANCS | Medium to long chain fatty acid glyceride | | Amphiphilic agent | | Preparation method |
| --- | --- | --- | --- | --- | --- | --- |
| 1 | 1 mg | Panasate 875 ® | 1 ml | phosphatidylcholine | 0.1 g | 1 |
| 2 | 1 mg | Panasate 810 ® | 0.95 ml | Unigli GO-206 ® | 0.05 ml | 2 |
| 3 | 1 mg | Panasate 800 ® olive oil | 0.25 ml 0.75 ml | yolk lecithin | 0.1 g | 1 |
| 4 | 1 mg | O.D.O. ® safflower oil | 0.25 ml 0.75 ml | soybean lecithin | 0.1 g | 1 |
| 5 | 1 mg | Panasate 875 ® | 0.95 ml | phosphatidylethanolamine Unigli GO-206 ® | 2 mg 0.05 ml | 2 |
| 6 | 1 mg | Panasate 875 ® Homoteks PT ® | 0.8 ml 0.2 ml | phosphatidylcholine | 2 mg | 2 |
| 7 | 1 mg | O.D.O ® containing 10% ethanol | 1 ml | yolk lecithin | 2 mg | 2 |
| 8 | 1 mg | Panasate 810 ® | 0.95 ml | phosphatidylcholine Unigli GO-206 ® | 0.1 g 0.05 ml | 2 |
| 9 | 1 mg | O.D.O. ® | 1 ml | soybean lecithin PEG6000 | 0.1 g 0.1 g | 2 |
| 10 | 1 mg | Panasate 800 ® | 0.9 ml | Tween 20 ® Span 20 ® | 0.05 ml 0.05 ml | 2 |
| 11 | 1 mg | O.D.O. ® | 1 ml | — | | 1 |
| 12 | 1 mg | Panasate 800 ® | 1 ml | — | | 1 |
| 13 | 1 mg | Panasate 810 ® | 1 ml | — | | 1 |
| 14 | 1 mg | safflower oil | 1 ml | — | | 1 |
| 15 | 1 mg | olive oil | 1 ml | — | | 1 |
| 16 | 1 mg | Panasate 875 ® | 1 ml | — | | 1 |
| 17 | 1 mg | edible oil (made by Nisshin Seiyu K.K.) | 1 ml | — | | 1 |
| 18 | 1 mg | O.D.O ® edible oil (made by Nisshin Seiyu K.K.) | 0.5 ml 0.5 ml | — | | 1 |
| 19 | 1 mg | O.D.O. ® edible oil (made by Nisshin Seiyu K.K.) | 0.5 ml 0.5 ml | phosphatidylcholine | 0.1 mg | 2 |
| 20 | 1 mg | O.D.O. ® | 0.95 ml | Azone ® | 0.05 ml | 2 |

TABLE 6-continued

| Preparation Example No. | BU-SMANCS | Medium to long chain fatty acid glyceride | | Amphiphilic agent | | Preparation method |
|---|---|---|---|---|---|---|
| 21 | 0.1 mg | O.D.O. ® | 1 ml | — | | 1 |
| 22 | 10 mg | O.D.O. ® | 1 ml | — | | 1 |
| 23 | 20 mg | O.D.O. ® | 1 ml | — | | 1 |
| 24 | 30 mg | O.D.O. ® | 1 ml | — | | 1 |
| 25 | 1 mg | Panasate 875 ® containing 10% ethanol | 0.95 ml | phosphatidylethanolamine Unigli GO-206 ® | 2 mg 0.05 ml | 2 |
| 26 | 1 mg | Panasate 875 ® containing 5% ethanol Homoteks PT ® | 0.8 ml 0.2 ml | phosphatidylcholine | 2 mg | 2 |
| 27 | 1 mg | Panasate 810 ® containing 15% ethanol | 0.95 ml | phosphatidylethanolamine Unigli GO-206 ® | 0.1 g 0.05 ml | 2 |

Preparation Example 28

4 mg of Bu-SMANCS and 8 mg of phosphatidylcholine as an amphiphilic agent were mixed in water and then lyophilized. The resulting lyophilized powder was added to 1 ml of Panasate 875 ® (medium chain fatty acid glyceride) containing 0.05 ml of Unigli GO-206 ® (amphiphilic agent, polyglycerine (6) dioleate) and uniformly dispersed thereinto by the ultrasonic treatment in ice.

Preparation Comparative Example 4 mg of Bu-SMANCS and 8 mg of phosphatidylcholine as an amphiphilic agent were mixed in water and then lyophilized. The resulting lyophilized powder was added to 1 ml of Lipiodol Ultra-Fluide ® (iodized poppy seed oil fatty acid ethylester) containing 0.05 ml of Unigli GO-206 ® (amphiphilic agent, polyglycerine (6) dioleate) and uniformly dispersed thereinto by the ultrasonic treatment in ice.

What is claimed is:

1. A composition for oral administration, consisting essentially of:
a neocarzinostatin derivative;
from 0.1 to 100 ml per mg of said neocarzinostatin derivative of at least one fatty acid glyceride which has from 6 to 20 carbon atoms and which is non-iodized; and
at least one amphiphilic agent present in an amount of from 0.01 to 0.1 ml, if liquid, or from 0.05 to 5 mg, if solid, per mg of said neocarzinostatin derivative,
wherein said neocarzinostatin derivative is represented by the following formula:

(SMA)—(NCS)—(SMA), wherein (NCS) is a divalent neocarzinostatin residue in which one hydrogen atom is removed from each primary amino group in an alanine residue at the N-terminal of neocarzinostatin and in a lysine residue at the 20th position from the N-terminal of neocarzinostatin, and (SMA) is a monovalent styrene-maleic acid copolymeric residue at least a portion of which may be half-esterified and which consists of structure units for
1) a styrene residue

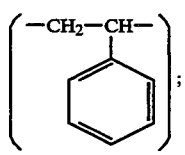

2) a residue having the following formula in which a hydroxy group of a one carboxyl group in a maleic acid residue is removed to leave a carbonyl group and is bonded to the neocarzinostatin residue

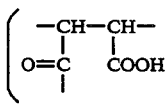

wherein the carbonyl group bonds to the neocarzinostatin residue via its carbon atom); and
3), a) a maleic acid residue

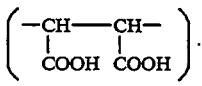

or b) a half-esterified maleic acid residue

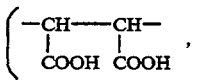

in which R is (i) an alcohol residue in which a hydroxyl group is removed from an alkanol having 1 to 4 carbon atoms, (ii) an ethylene glycol monoalkyl ether in which the alkyl group has 1 to 2 carbon atoms, or (iii) a glycerine dialkyl ether in which the alkyl group has 1 to 2 carbon atoms), and a maleic acid residue

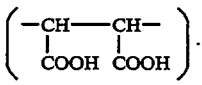

2. The composition according to claim 1, wherein each said monovalent styrene-maleic acid copolymeric residue is a half-esterified maleic acid residue, wherein R is said alcohol residue in which a hydroxyl group is removed from an alkanol, and wherein said alkanol has 4 carbon atoms and is a butyl group.

3. The composition according to claim 1, wherein said at least one fatty acid glyceride is selected from the group consisting of caprylic acid triglycerides, capric acid triglycerides and a mixture thereof.

4. The composition according to claim 1, wherein the at least one amphiphilic agent is selected from the group consisting of a natural ampholytic surfactant, a fatty acid ester, and a polyethylene glycol.

* * * * *